US006913913B2

(12) United States Patent
Cheung (10) Patent No.: US 6,913,913 B2
(45) Date of Patent: *Jul. 5, 2005

(54) METHODS AND COMPOSITIONS FOR TREATING RENAL FAILURE

(75) Inventor: Ling Yuk Cheung, Hong Kong (HK)

(73) Assignee: Ultra Biotech Limited, Douglas (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/717,135

(22) Filed: Nov. 18, 2003

(65) Prior Publication Data

US 2005/0106169 A1 May 19, 2005

(51) Int. Cl.[7] .............................. C12N 1/14; C12N 13/00
(52) U.S. Cl. ................................. 435/173.1; 435/255.1; 435/255.2; 435/173.8
(58) Field of Search .......................... 435/173.1, 255.1, 435/255.2, 173.8, 294.2, 294.21; 424/195.16

(56) References Cited

U.S. PATENT DOCUMENTS

| | | |
|---|---|---|
| 2,107,830 A | 2/1938 | Liebesny et al. |
| 3,150,979 A | 9/1964 | Ensley |
| 3,711,392 A | 1/1973 | Metzger |
| 3,870,599 A | 3/1975 | Azarowicz |
| 3,923,279 A | 12/1975 | Gresley et al. |
| 3,939,279 A | 2/1976 | Kawano et al. |
| 3,968,254 A | 7/1976 | Rhodes et al. |
| 3,997,675 A | 12/1976 | Eichelburg |
| 4,041,182 A | 8/1977 | Erickson et al. |
| 4,081,367 A | 3/1978 | Hulls et al. ................. 210/610 |
| 4,118,512 A | 10/1978 | Eichelburg |
| 4,183,807 A | 1/1980 | Yoshizawa et al. ......... 210/611 |
| 4,211,645 A | 7/1980 | Zajic et al. ................. 210/611 |
| 4,348,483 A | 9/1982 | Skogerson |
| 4,559,305 A | 12/1985 | Zajic et al. ................. 435/243 |
| 4,816,158 A | 3/1989 | Shimura et al. ............ 210/610 |

(Continued)

FOREIGN PATENT DOCUMENTS

| | | |
|---|---|---|
| CN | 1110317 A | 10/1995 |
| CN | 1207873 | 2/1999 |
| CN | 1309175 | 8/2001 |
| EP | 0041373 | 12/1981 |
| EP | 553377 | 8/1993 |
| EP | 1375652 | 1/2004 |
| ES | 475500 | 4/1979 |
| FR | 2222433 | 10/1974 |
| GB | 1397873 | 6/1975 |
| JP | 60028893 | 2/1985 |
| SU | 415983 A | 11/1974 |

(Continued)

OTHER PUBLICATIONS

Agarwal N. et al., "Selection of *Saccharomyces cerevisiae* strains for use as a microbial feed additive," *Letters in Applied Microbiology*, 31:270–273 (2000).

Asami, K. et al., "Real–Time Monitoring of Yeast Cell Division by Dielectric Spectroscopy", *Biophysical Journal*, 76, pp. 3345–3348 (1999).

(Continued)

*Primary Examiner*—Christopher R. Tate
*Assistant Examiner*—Randall Winston
(74) *Attorney, Agent, or Firm*—Fish & Neave IP Group Ropes & Gray LLP; James F. Halay, Jr.; Z. Ying Li (57) ABSTRACT

Compositions comprising a plurality of yeast cells, wherein said plurality of yeast cells are characterized by their ability to ameliorate renal failure (e.g., improved diuretic effect and/or lowering blood urea nitrogen, proteinuria, and/or serum creatinine levels) in a subject as a result of having been cultured in the presence of an alternating electric field having a specific frequency and a specific field strength. Also included are methods of making and using such compositions.

11 Claims, 2 Drawing Sheets

U.S. PATENT DOCUMENTS

| | | |
|---|---|---|
| 5,047,250 A | 9/1991 | Prieels et al. |
| 5,075,008 A | 12/1991 | Chigusa et al. ............. 210/610 |
| 5,082,662 A | 1/1992 | Laurent et al. |
| 5,082,936 A | 1/1992 | Jamas et al. |
| 5,106,594 A | 4/1992 | Held et al. .................. 422/292 |
| 5,158,788 A | 10/1992 | Lavens et al. |
| 5,416,010 A | 5/1995 | Langenberg et al. ........ 435/468 |
| 5,476,787 A | 12/1995 | Yokoyama et al. ...... 435/262.5 |
| 5,504,079 A | 4/1996 | Jamas et al. |
| 5,567,314 A | 10/1996 | Chigusa et al. ............. 210/150 |
| 5,578,486 A | 11/1996 | Zhang ........................ 435/243 |
| 5,665,352 A | 9/1997 | Blehaut et al. |
| 5,707,524 A | 1/1998 | Potter ........................ 210/606 |
| 5,866,116 A | 2/1999 | Yaegaki |
| 5,879,928 A | 3/1999 | Dale et al. .................. 435/264 |
| 5,952,020 A | 9/1999 | Lizak |
| 5,981,219 A | 11/1999 | Flugge et al. |
| 6,036,854 A | 3/2000 | Potter ........................ 210/177 |
| 6,045,834 A | 4/2000 | Howes et al. |
| 6,143,731 A | 11/2000 | Jamas et al. |
| 6,159,510 A | 12/2000 | Lizak |
| 6,197,295 B1 | 3/2001 | Hsia et al. |
| 6,214,337 B1 | 4/2001 | Hayen et al. |
| 6,391,617 B1 | 5/2002 | Cheung ...................... 435/254 |
| 6,391,618 B1 | 5/2002 | Cheung ...................... 435/255 |
| 6,391,619 B1 | 5/2002 | Cheung ...................... 435/255 |
| 6,416,982 B1 | 7/2002 | Zhang |
| 6,416,983 B1 | 7/2002 | Cheung |
| 6,436,695 B1 | 8/2002 | Cheung ...................... 435/254 |
| 6,440,713 B1 | 8/2002 | Cheung ...................... 435/173 |
| 6,596,272 B2 | 7/2003 | Cheung |
| 6,596,273 B2 | 7/2003 | Cheung |
| 6,649,383 B1 | 11/2003 | Cheung ................... 435/173.1 |
| 6,660,508 B1 | 12/2003 | Cheung ................... 435/173.1 |
| 6,699,496 B1 | 3/2004 | Kojima et al. |
| 6,761,886 B2 | 7/2004 | Cheung |
| 6,800,466 B2 | 10/2004 | Cheung |
| 6,828,131 B2 | 12/2004 | Zhang |
| 6,828,132 B2 | 12/2004 | Cheung |
| 2002/0099026 A1 | 7/2002 | Goodman et al. |
| 2002/0123127 A1 | 9/2002 | Cheung ...................... 435/254 |
| 2002/0123129 A1 | 9/2002 | Cheung ...................... 435/254 |
| 2002/0123130 A1 | 9/2002 | Cheung ...................... 435/262 |
| 2003/0230126 A1 | 12/2003 | Cheung |
| 2003/0230245 A1 | 12/2003 | Cheung |
| 2003/0232038 A1 | 12/2003 | Cheung |
| 2003/0232039 A1 | 12/2003 | Cheung |
| 2003/0232059 A1 | 12/2003 | Cheung |
| 2003/0235565 A1 | 12/2003 | Cheung |
| 2003/0235566 A1 | 12/2003 | Cheung |
| 2003/0235567 A1 | 12/2003 | Cheung |
| 2003/0235568 A1 | 12/2003 | Cheung |
| 2003/0235569 A1 | 12/2003 | Cheung |
| 2003/0235570 A1 | 12/2003 | Cheung |
| 2004/0001812 A1 | 1/2004 | Cheung |
| 2004/0001813 A1 | 1/2004 | Cheung |
| 2004/0001814 A1 | 1/2004 | Cheung |
| 2004/0001815 A1 | 1/2004 | Cheung .................. 424/93.51 |
| 2004/0001857 A1 | 1/2004 | Cheung ................ 424/195.16 |
| 2004/0001858 A1 | 1/2004 | Cheung ................ 424/195.16 |
| 2004/0001859 A1 | 1/2004 | Cheung ................ 424/195.16 |
| 2004/0001860 A1 | 1/2004 | Cheung ................ 424/195.16 |
| 2004/0001861 A1 | 1/2004 | Cheung ................ 424/195.16 |
| 2004/0005335 A1 | 1/2004 | Cheung |
| 2004/0005337 A1 | 1/2004 | Cheung ................ 424/195.16 |
| 2004/0005680 A1 | 1/2004 | Cheung |
| 2004/0168492 A1 | 9/2004 | Cheung |
| 2004/0253251 A1 | 12/2004 | Cheung |
| 2004/0253252 A1 | 12/2004 | Cheung |
| 2004/0253253 A1 | 12/2004 | Cheung |
| 2004/0253254 A1 | 12/2004 | Cheung |
| 2004/0253255 A1 | 12/2004 | Cheung |
| 2004/0253256 A1 | 12/2004 | Cheung |
| 2004/0253257 A1 | 12/2004 | Cheung |
| 2004/0253258 A1 | 12/2004 | Cheung |
| 2004/0253259 A1 | 12/2004 | Cheung |
| 2004/0253260 A1 | 12/2004 | Cheung |
| 2004/0253261 A1 | 12/2004 | Cheung |
| 2004/0253262 A1 | 12/2004 | Cheung |
| 2004/0253263 A1 | 12/2004 | Cheung |
| 2004/0253264 A1 | 12/2004 | Cheung |
| 2004/0253265 A1 | 12/2004 | Cheung |
| 2004/0253266 A1 | 12/2004 | Cheung |
| 2004/0253267 A1 | 12/2004 | Cheung |
| 2004/0253268 A1 | 12/2004 | Cheung |
| 2004/0265990 A1 | 12/2004 | Cheung |

FOREIGN PATENT DOCUMENTS

| | | |
|---|---|---|
| SU | 1071637 | 2/1984 |
| SU | 1722364 | 3/1992 |
| SU | 1750570 | 7/1992 |
| WO | WO 87/02705 | 5/1987 |
| WO | WO 95/04814 | 2/1995 |
| WO | WO 99/60142 | 11/1999 |
| WO | WO 02/20431 | 3/2002 |
| WO | WO 02/62981 | 8/2002 |
| WO | WO 02/62982 | 8/2002 |
| WO | WO 02/62983 | 8/2002 |
| WO | WO 02/62984 | 8/2002 |
| WO | WO 02/62985 | 8/2002 |
| WO | WO02070436 | 9/2002 |
| WO | WO 02/070682 A2 | 9/2002 |
| WO | WO02070683 | 9/2002 |
| WO | WO2004108919 | 12/2004 |

OTHER PUBLICATIONS

Balcer–Kubiczek, E.K. et al., "Expression Analysis of Human HL60 Cells Exposed to 60 Hz Square–or Sine–Wave Magnetic Fields", *Radiation Research*, 153, pp. 670–678 (2000).

Bassett, C.A.L. et al., "Beneficial Effects of Electromagnetic Fields", *Journal of Cellular Biochemistry*, 51, pp. 387–393 (1993).

Binninger, D. M. et al., "Effects of 60Hz AC magnetic fields on gene expression following exposure over multiple cell generations using *Saccharomyces cerevisiae*", *Bioelectrochemistry and Bioenergetics*, 43(1): 83–89 (1997).

Conti, P. et al., "Effect of Electromagnetic Fields on Several CD Markers and Transcription and Expression of CD4", *Immunobiology*, 201, pp. 36–48 (1999).

Deguchi, T. et al., "Nylon biodegradation by lignin–degrading fungi", *Applied and Environmental Microbiology*, 63(1): 329–331 (1997).

Dufresne C. et al., "Tea, Kombucha, and Health; A review," *Food Research International*, 33:409–421 (2000).

Gonzalez, A.M. et al., "Effects of an Electric Field of Sinusoidal Waves on the Amino Acid Biosynthesis by Azotobacter", *Z. Naturforsch*, 35, pp. 258–261 (1980).

Goodman, E.M. et al., "Effects of Electromagnetic Fields on Molecules and Cells", *International Review of Cytology*, 158, pp. 279–339 (1995).

Greenwalt C.J. et al., "Kombucha, the fermented tea: Microbiology, composition, and claimed health effects," *Journal of Food Protection*, 63:976–981 (2000).

Grospietsch, T. et al., "Stimulating Effects of Modulated 150 MHz Electromagnetic Fields and the Growth of *Escherichia coli* in a Cavity Resonator", *Bioelectrochemistry and Bioenergetics*, 37, pp. 17–23 (1995).

Grundler W. et al., "Resonant–like dependence at yeast growth rate on microwave frequencies," *The British Journal of Cancer*, Supplement, England Mar. 1982, 45:206–208 (1982).

Grundler, W. et al., "Mechanisms of Electromagnetic Interaction with Cellular Systems", *Naturwissenschaften*, 79, pp. 551–559 (1992).

Grundler, W. et al., "Nonthermal Effects of Millimeter Microwaves on Yeast Growth", *Z. Naturforsch*, 33, pp. 15–22 (1978).

Ivaschuk, O.I. et al., "Exposure of Nerve Growth Factor–Treated PC12 Rat Pheochromocytoma Cells to a Modulated Radiofrequency Field at 836.55 MHz: Effects on c–jun and c–fos Expression", *Bioelectromagnetics*, 18, pp. 223–229 (1997).

Jelinek, F. et al., "Microelectronic Sensors for Measurement of Electromagnetic Fields of Living Cells and Experimental Results", *Bioelectrochemistry and Bioenergetics*, 48, pp. 261–266 (1999).

Lacy–Hulbert, A. et al., "Biological Responses to Electromagnetic Fields", *FASEB Journal*, 12, pp. 395–420 (1998).

Libertin, C.R. et al., "Effects of Gamma Rays, Ultraviolet Radiation, Sunlight, Microwaves and Electromagnetic Fields on Gene Expression Mediated by Human Immunodeficiency Virus Promoter", *Radiation Research*, 140, pp. 91–96 (1994).

Lin, H. et al., "Magnetic Field Activation of Protein–DNA Binding", *Journal of Cellular Biochemistry*, 70, pp. 297–303 (1998).

Lin, H. et al., "Specific Region of the c–myc Promoter Is Responsive to Electric and Magnetic Fields", *Journal of Cellular Biochemistry*, 54, pp. 281–288 (1994).

Liu C.H. et al., "The Isolation and identification of microbes from a fermented tea beverage, Haipao, and their interactions during Haipao fermentation," *Food Microbiology* (London), 13:407–415 (1996).

Loberg, L.I. et al., "Expression of Cancer–Related Genes in Human Cells Exposed to 60 Hz Magnetic Fields", *Radiation Research*, 153, pp. 679–684 (2000).

Mayser P. et al., "The yeast spectrum of the 'tea fungus Kombucha'," *Mycoses*, Blackwell, Berlin, Germany, 38:289–295 (1995).

Moore, R.L., "Biological Effects of Magnetic Fields: Studies with Microorganisms", *Canadian Journal of Microbiology*, 25, pp. 1145–1151 (1979).

Morehouse, C.A. et al., "Exposure of Daudi Cells to Low–Frequency Magnetic Fields Does Not Elevate MYC Steady–State mRNA Levels", *Radiation Research*, 153, pp. 663–669 (2000).

Norris, V. et al., "Do Bacteria Sing? Sonic Intercellular Communication Between Bacteria May Reflect Electromagnetic Intracellular Communication Involving Coherent Collective Vibrational Modes that Could Integrate Enzyme Activities and Gene Expression", *Molecular Microbiology*, 24, pp. 879–880 (1997).

Novelli, G. et al., "Study of the Effects on DNA of Electromagnetic Fields Using Clamped Homogeneous Electric Field Gel Electrophoresis", *Biomedicine & Pharmacotherapy*, 45, pp. 451–454 (1991).

Phillips, J.L., "Effects of Electromagnetic Field Exposure on Gene Transcription", *Journal of Cellular Biochemistry*, 51, pp. 381–386 (1993).

Pichko, V. B. et al., "Electromagnetic stimulation of productivity of microorganisms and its mechanisms", *Prikladnaya Biokhimiya I Mikrobiologiya*, 32(4): 468–472 (1996).

Ponne, C. T. et al., "Interaction of electromagnetic energy with biological material—relation to food processing", *Radiation Physics and Chemistry*, 45(4): 591–607 (1995).

Romano–Spica, V. et al., "Ets1 Oncogene Induction by ELF–Modulated 50 MHz Radiofrequency Electromagnetic Field", *Bioelectromagnetics*, 21, pp. 8–18 (2000).

Surawicz Christina M. et al., "The search for a better treatment for recurrent Clostridium difficile disease: Use of high–dose vancomycin combined with *Saccharomyces boulardii*," *Clinical Infectious Diseases*, 31:1012–1017 (2000).

Trosko, J.E., "Human Health Consequences of Environmentally–Modulated Gene Expression: Potential Roles of ELF–EMF Induced Epigenetic Versus Mutagenic Mechanisms of Disease", *Bioelectromagnetics*, 21, pp. 402–406 (2000).

Van den Bogaerde J. et al., "Immune sensitization to food, yeast and bacteria in Crohn's disease," *Alimentary Pharmacology & Therapeutics*, 15:1647–1653 (2001).

Van Rensburg, P. et al., "Engineering yeast for efficient cellulose degradation", *Yeast*, 14(1): 67–76 (1998).

Ventura, C. et al., "Elf–pulsed Magnetic Fields Modulate Opioid Peptide Gene Expression in Myocardial Cells", *Cardiovascular Research*, 45, pp. 1054–1064 (2000).

Woodward, A.M. et al., "Genetic Programming as an Analytical Tool for Non–linear Dielectric Spectroscopy", *Bioelectrochemistry and Bioenergetics*, 48, pp. 389–396 (1999).

Yonetani, T. et al., "Electromagnetic Properties of Hemoproteins", *The Journal of Biological Chemistry*, 247, pp. 2447–2455 (1972).

Zhang, L. et al., "Electrostimulation of the Dehydrogenase System of Yeast by Alternating Currents", *Bioelectrochemistry and Bioenergetics*, 28, pp. 341–353 (1992).

"*Saccharomyces cerevisiae* Meyen ex Hansen", China Catalogue of Cultures/China Committee of Culture Collection for Microorganisms (CCCCM), "www.im.ac.cn/database/YEAST/y122.htm", Apr. 24, 1996, retrieved on Nov. 27, 2002.

U.S. Appl. No. 10/192,805 filed Nov. 29, 2004, Zhang.

U.S. Appl. No. 10/192,807 filed Nov. 29, 2004, Cheung.

Born et al., "The Saccharomyces *Boulardil* Therapy of HIV–Associated Diarrhea", Deutsche Medizinische Wochenschriff, 118(20):765 (1993). (in German with English translation).

Dutta et al., *J. of Microwave Power*, vol. 14, No. 3, pp. 275–280 (1979).

Goodman, et al., "Magnetic Field Stress Induces Expression of *HSP70*", *Cell Stress & Chaperones* 3(2):79–88 (1998).

Grundler W., "Resonant Microwave Effect on Locally Fixed Yeast Microcolonies" *Z. Naturforsch* 44c:863–866 (1989).

Kim et al., "Anti–Stress and Anti–Fatigue Effects on Fermented Rice Bran", *Biosci Biotechnol Biochem.*, 65(10):2294–6 (2001).

Lin H. et al., "A Magnetic Field–Responsive Domain in the Human HSP70 Promoter", *J. Cell Biochem*, 75:170–176 (1999).

Machado Caetano et al., "Immunopharmacological Effects of *Sacchoramyces Boulardil* in Healthy Human Volunteers", *Int'l Immunology and Immunopathology*, 8(3):245–259 (1986).

Ortuno et al., "Oral Administration of Yeast, *Saccharomyces Cerevisiae*, Enhances the Cellular Innate Immune response of Gilthead Seabream (*Sparus aurate L.*)", *Vet Immunol Immunopathol*, 85(1–2):41–50 (2002).

Peret Filho et al., "Dose Effect of Oral Saccharomyces *Boulardil* Treatments on Morbidity and Mortality in Immunosuppressed Mice", *J Med Microbiol.*, 47(2):111–6 (1998).

Saha et al., "Microbial Manipulation of Rumen Fermentation Using *Saccharomyces Cerevisiae* as Probiotics", *Current Science (Bangalore)*, 77(5):696–697 (1999).

WHO World Health Organization; WebPages *http:www.who.int/peh–emf/about/WhatisEMF/en/and http:www.who.int/peh–emf/about/WhatisEMF/en/index3.html retrieved Jun. 10, 2004.*

METHODS AND COMPOSITIONS FOR TREATING RENAL FAILURE

FIELD OF THE INVENTION

The invention relates to compositions that can improve renal function and are useful as dietary supplements (e.g., health drinks) or medication. These compositions contain yeast cells obtainable by growth in electromagnetic fields with specific frequencies and field strengths.

BACKGROUND OF THE INVENTION

Renal failure is a disease state in which renal functions are damaged severely such that internal environment of the living body can no longer be maintained in normal conditions. In particular, acute renal failure involves a sudden loss of the kidneys' ability to excrete wastes, concentrate urine, and conserve electrolytes. Causes of acute renal failure include acute tubular necrosis (ATN), myoglobinuria (myoglobin in the urine), infections such as acute pyelonephritis or septicemia, urinary tract obstruction such as a narrowing of the urinary tract (stricture), tumor, kidney stones, nephrocalcinosis, enlarged prostate with subsequent acute bilateral obstructive uropath, severe acute nephritic syndrome, disorders of the blood, malignant hypertension, and autoimmune disorders such as scleroderma. Other causes such as poisons and trauma, for example a direct and forceful blow to the kidneys, can also lead to renal failure.

Chronic renal failure is a gradual loss of kidney functions and usually occurs over a number of years as the internal structures of the kidney are slowly destroyed. Causative diseases include glomerulonephritis of any type, polycystic kidney disease, diabetes mellitus, hypertension, Alport syndrome, reflux nephropathy, obstructive uropathy, kidney stones and infection, and analgesic nephropathy. Chronic renal failure results in the accumulation of fluid and waste products in the body, causing azotemia and uremia.

Therapeutic agents for acute renal failure include loop diuretics and osmotic diuretics, which are used in expectation of recovery of renal functions by increasing the flow in kidney tubules so as to wash away casts formed in the tubules and thereby prevent obstruction of the tubules. Agents for chronic renal failure include imidazole angiotensin-II (AII) receptor antagonists and anipamil. However, depending on the manner of use, these agents present the risk of inviting hearing disorders and the even more severe adverse side effects of heart failure and pulmonary edema.

SUMMARY OF THE INVENTION

This invention is based on the discovery that certain yeast cells can be activated by electromagnetic fields having specific frequencies and field strengths to produce substances useful in ameliorating renal failure. Compositions comprising these activated yeast cells can be used as medication or as dietary supplements, in the form of health drinks or dietary pills (tablets or powder). For instance, these compositions can be used to treat renal failure in a subject (e.g., a human subject) as indicated by their improved diuretic effect and/or lowered blood urea nitrogen, proteinuria, and/or serum creatinine levels.

This invention embraces a composition comprising a plurality of yeast cells that have been cultured in an alternating electric field having a frequency in the range of about 9500 to 13000 MHz (e.g., 9750–10500, 12000–12500 and/or 12600–12980 MHz) and a field strength in the range of about 220 to 480 mV/cm (e.g., 250–270, 260–280, 280–305, 290–310, 315–335, 325–345, 350–370, 370–390, 380–400, 380–420, and/or 430–450 mV/cm). The yeast cells are cultured for a period of time sufficient to activate said plurality of yeast cells to treat kidney diseases in a subject. In one embodiment, the frequency and/or the field strength of the alternating electric field can be altered within the aforementioned ranges during said period of time. In other words, the yeast cells are exposed to a series of electromagnetic fields. An exemplary period of time is about 130–230 hours (e.g., 169–193 hours).

Also included in this invention is a composition comprising a plurality of yeast cells that have been cultured under acidic conditions in an alternating electric field having a frequency in the range of about 12000 to 13000 MHz (e.g., 12500–13000 MHz) and a field strength in the range of about 300 to 420 mV/cm (e.g., 350–370 and/or 370–390 mV/cm). In one embodiment, the yeast cells are exposed to a series of electromagnetic fields. An exemplary period of time is about 50–100 hours (e.g., 57–73 hours).

Yeast cells that can be included in this composition can be derived from parent strains publically available from the China General Microbiological Culture Collection Center ("CGMCC"), China Committee for Culture Collection of Microorganisms, Institute of Microbiology, Chinese Academy of Sciences, Haidian, P.O. Box 2714, Beijing, 100080, China. Useful yeast species include, but are not limited to, those commonly used in food and pharmaceutical industries, such as *Saccharomyces cerevisiae* (e.g., Hansen and Hansen Var. *ellipsoideus*), *Saccharomyces carlsbergensis*, *Saccharomyces rouxii*, *Saccharomyces sake*, *Saccharomyces uvarum*, *Saccharomyces sp.*, *Schizosaccharomyces pombe*, *Rhodotorula aurantiaca* and *Rhodotorula rubar*. For instance, the yeast cells can be of the strain *Saccharomyces cerevisiae* Hansen AS2.16, AS2.112 or AS2.504, *Saccharomyces sp.* AS2.311, *Schizosaccharomyces pombe* Lindner AS2.274, *Saccharomyces sake* Yabe ACCC2045, *Saccharomyces uvarum* Beijer IFFI1207, *Saccharomyces rouxii* Boutroux AS2.370, *Saccharomyces cerevisiae* Hansen Var. *ellipsoideus* AS2.612, *Saccharomyces carisbergensis* Hansen AS2.417, or *Rhodotorula rubar* (Demme) Lodder AS2.105. Other useful yeast strains are illustrated in Table 1.

This invention further embraces a composition comprising a plurality of yeast cells, wherein said plurality of yeast cells have been activated to treat kidney diseases in a subject. Included in this invention are also methods of making the above compositions.

As used herein, a subject includes a human and veterinary subject.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. The materials, methods, and examples are illustrative only and not intended to be limiting. Throughout this specification and claims, the word "comprise," or variations such as "comprises" or "comprising" will be understood to imply the inclusion of a stated integer or group of integers but not the exclusion of any other integer or group of integers.

DETAILED DESCRIPTION OF THE INVENTION

This invention is based on the discovery that certain yeast strains can be activated by electromagnetic fields ("EMF") having specific frequencies and field strengths to become highly efficient in producing substances that restore urine secretion and/or lower blood urea nitrogen, proteinuria and/or serum creatinine levels in a subject. Compositions containing these activated yeast cells are thus useful in treating kidney diseases. Yeast compositions containing activated yeast cells can be used as medication or as dietary supplements, in the form of health drinks or dietary pills (tablets or powder).

Since the activated yeast cells contained in the yeast compositions have been cultured to endure acidic conditions (pH 2.5–4.2), these cells can survive the gastric environment and pass on to the intestines. Once in the intestines, the yeast cells are ruptured by various digestive enzymes, and the active substances in treatment of kidney diseases are released and readily absorbed.

I. Yeast Strains Useful in the Invention

The types of yeasts useful in this invention include, but are not limited to, yeasts of the genera *Saccharomyces, Schizosaccharomyces,* and *Rhodotorula.*

Exemplary species within the above-listed genera include, but are not limited to, those illustrated in Table 1. Yeast strains useful for this invention can be obtained from laboratory cultures, or from publically accessible culture depositories, such as CGMCC and the American Type Culture Collection, 10801 University Boulevard, Manassas, Va. 20110-2209. Non-limiting examples of useful strains (with accession numbers of CGMCC) are *Saccharomyces cerevisiae* Hansen AS2.16, AS2.112 and AS2.504, *Saccharomyces sp.* AS2.311, *Schizosaccharomyces pombe* Lindner AS2.274, *Saccharomyces sake* Yabe ACCC2045, *Saccharomyces uvarum* Beijer IFFI 1207, *Saccharomyces rouxii* Boutroux AS2.370, *Saccharomyces cerevisiae* Hansen Var. *ellipsoideus* AS2.612, *Saccharomyces carlsbergensis* Hansen AS2.417, and *Rhodotorula rubar* (Demme) Lodder AS2.105. Other useful yeast strains are illustrated in Table 1.

The preparation of the yeast compositions of this invention is not limited to starting with a pure strain of yeast. A yeast composition of the invention may be produced by culturing a mixture of yeast cells of different species or strains. The ability of any activated species or strain of yeasts to treat kidney diseases can be readily tested by methods known in the art. See, for instance, Examples 1 and 2.

TABLE 1

Exemplary Yeast Strains

*Saccharomyces cerevisiae* Hansen

| ACCC2034 | ACCC2035 | ACCC2036 | ACCC2037 | ACCC2038 |
|---|---|---|---|---|
| ACCC2039 | ACCC2040 | ACCC2041 | ACCC2042 | AS2.1 |
| AS2.4 | AS2.11 | AS2.14 | AS2.16 | AS2.56 |
| AS2.69 | AS2.70 | AS2.93 | AS2.98 | AS2.101 |
| AS2.109 | AS2.110 | AS2.112 | AS2.139 | AS2.173 |
| AS2.174 | AS2.182 | AS2.196 | AS2.242 | AS2.336 |
| AS2.346 | AS2.369 | AS2.374 | AS2.375 | AS2.379 |
| AS2.380 | AS2.382 | AS2.390 | AS2.393 | AS2.395 |
| AS2.396 | AS2.397 | AS2.398 | AS2.399 | AS2.400 |
| AS2.406 | AS2.408 | AS2.409 | AS2.413 | AS2.414 |
| AS2.415 | AS2.416 | AS2.422 | AS2.423 | AS2.430 |
| AS2.431 | AS2.432 | AS2.451 | AS2.452 | AS2.453 |
| AS2.458 | AS2.460 | AS2.463 | AS2.467 | AS2.486 |
| AS2.501 | AS2.502 | AS2.503 | AS2.504 | AS2.516 |
| AS2.535 | AS2.536 | AS2.558 | AS2.560 | AS2.561 |
| AS2.562 | AS2.576 | AS2.593 | AS2.594 | AS2.614 |
| AS2.620 | AS2.628 | AS2.631 | AS2.666 | AS2.982 |
| AS2.1190 | AS2.1364 | AS2.1396 | IFFI1001 | IFFI1002 |
| IFFI1005 | IFFI1006 | IFFI1008 | IFFI1009 | IFFI1010 |
| IFFI1012 | IFFI1021 | IFFI1027 | IFFI1037 | IFFI1042 |
| IFFI1043 | IFFI1045 | IFFI1048 | IFFI1049 | IFFI1050 |
| IFFI1052 | IFFI1059 | IFFI1060 | IFFI1062 | IFFI1063 |
| IFFI1202 | IFFI1203 | IFFI1206 | IFFI1209 | IFFI1210 |
| IFFI1211 | IFFI1212 | IFFI1213 | IFFI1214 | IFFI1215 |
| IFFI1220 | IFFI1221 | IFFI1224 | IFFI1247 | IFFI1248 |
| IFFI1251 | IFFI1270 | IFFI1277 | IFFI1287 | IFFI1289 |
| IFFI1290 | IFFI1291 | IFFI1292 | IFFI1293 | IFFI1297 |
| IFFI1300 | IFFI1301 | IFFI1302 | IFFI1307 | IFFI1308 |
| IFFI1309 | IFFI1310 | IFFI1311 | IFFI1331 | IFFI1335 |
| IFFI1336 | IFFI1337 | IFFI1338 | IFFI1339 | IFFI1340 |
| IFFI1345 | IFFI1348 | IFFI1396 | IFFI1397 | IFFI1399 |
| IFFI1411 | IFFI1413 | IFFI1441 | IFFI1443 | |

*Saccharomyces cerevisiae* Hansen Var.*ellipsoideus* (Hansen) Dekker

| ACCC2043 | AS2.2 | AS2.3 | AS2.8 | AS2.53 |
|---|---|---|---|---|
| AS2.163 | AS2.168 | AS2.483 | AS2.541 | AS2.559 |
| AS2.606 | AS2.607 | AS2.611 | AS2.612 | |

*Saccharomyces chevalieri* Guilliermond

| AS2.131 | AS2.213 |
|---|---|

*Saccharomyces delbrueckii*

| AS2.285 |
|---|

*Saccharomyces delbrueckii* Lindner ver.*mongolicus* (Saito) Lodder et van Rij

| AS2.209 | AS2.1157 |
|---|---|

*Saccharomyces exiguous* Hansen

| AS2.349 | AS2.1158 |
|---|---|

*Saccharomyces fermentati* (Saito) Lodder et van Rij

| AS2.286 | AS2.343 |
|---|---|

*Saccharomyces logos* van laer et Denamur ex Jorgensen

| AS2.156 | AS2.327 | AS2.335 |
|---|---|---|

*Saccharomyces mellis* (Fabian et Quinet) Lodder et kreger van Rij

| AS2.195 |
|---|

*Saccharomyces mellis* Microellipsoides Osterwalder

| AS2.699 |
|---|

*Saccharomyces oviformis* Osteralder

| AS2.100 |
|---|

*Saccharomyces rosei* (Guilliermond) Lodder et Kreger van Rij

| AS2.287 |
|---|

*Saccharomyces rouxii* Boutroux

| AS2.178 | AS2.180 | AS2.370 | AS2.371 |
|---|---|---|---|

TABLE 1-continued

Exemplary Yeast Strains

*Saccharomyces sake* Yabe

ACCC2045

*Candida arborea*

AS2.566

*Candida lambica* (Lindner et Genoud) van.Uden et Buckley

AS2.1182

*Candida krusei* (Castellani) Berkhout

AS2.1045

*Candida lipolytica* (Harrison) Diddens et Lodder

| AS2.1207 | AS2.1216 | AS2.1220 | AS2.1379 | AS2.1398 |
|---|---|---|---|---|
| AS2.1399 | AS2.1400 | | | |

*Candida parapsilosis* (Ashford) Langeron et Talice Var.*intermedia* Van Rij et Verona

AS2.491

*Candida parapsilosis* (Ashford) Langeron et Talice

AS2.590

*Candida pulcherrima* (Lindner) Windisch

AS2.492

*Candida rugousa* (Anderson) Diddens et Lodder

| AS2.511 | AS2.1367 | AS2.1369 | AS2.1372 | AS2.1373 |
|---|---|---|---|---|
| AS2.1377 | AS2.1378 | AS2.1384 | | |

*Candida tropicalis* (Castellani) Berkhout

| ACCC2004 | ACCC2005 | ACCC2006 | AS2.164 | AS2.402 |
|---|---|---|---|---|
| AS2.564 | AS2.565 | AS2.567 | AS2.568 | AS2.617 |
| AS2.637 | AS2.1387 | AS2.1397 | | |

*Candida utilis* Henneberg Lodder et Kreger Van Rij

AS2.120  AS2.281  AS2.1180

*Crebrothecium ashbyii* (Guillermond) Routein (*Eremothecium ashbyii* Guilliermond)

AS2.481  AS2.482  AS2.1197

*Geotrichum candidum* Link

| ACCC2016 | AS2.361 | AS2.498 | AS2.616 | AS2.1035 |
|---|---|---|---|---|
| AS2.1062 | AS2.1080 | AS2.1132 | AS2.1175 | AS2.1183 |

*Hansenula anomala* (Hansen)H et P sydow

| ACCC2018 | AS2.294 | AS2.295 | AS2.296 | AS2.297 |
|---|---|---|---|---|
| AS2.298 | AS2.299 | AS2.300 | AS2.302 | AS2.338 |
| AS2.339 | AS2.340 | AS2.341 | AS2.470 | AS2.592 |
| AS2.641 | AS2.642 | AS2.782 | AS2.635 | AS2.794 |

*Hansenula arabitolgens* Fang

AS2.887

*Hansenula jadinii* (A.et R Sartory Weill et Meyer) Wickerham

ACCC2019

*Hansenula saturnus* (Klocker) H et P sydow

ACCC2020

*Hansenula schneggii* (Weber) Dekker

AS2.304

*Hansenula subpelliculosa* Bedford

| AS2.740 | AS2.760 | AS2.761 | AS2.770 | AS2.783 |
|---|---|---|---|---|
| AS2.790 | AS2.798 | AS2.866 | | |

*Kloeckera apiculata* (Reess emend.Klocker) Janke

| ACCC2022 | ACCC2023 | AS2.197 | AS2.496 | AS2.714 |
|---|---|---|---|---|
| ACCC2021 | AS2.711 | | | |

*Lipomyces starkeyi* Lodder et van Rij

AS2.1390  ACCC2024

*Pichia farinosa* (Lindner) Hansen

| ACCC2025 | ACCC2026 | AS2.86 | AS2.87 | AS2.705 |
|---|---|---|---|---|
| AS2.803 | | | | |

*Pichia membranaefaciens* Hansen

ACCC2027  AS2.89  AS2.661  AS2.1039

*Rhodosporidium toruloides* Banno

ACCC2028

*Rhodotorula glutinis* (Fresenius) Harrison

| AS2.2029 | AS2.280 | ACCC2030 | AS2.102 | AS2.107 |
|---|---|---|---|---|
| AS2.278 | AS2.499 | AS2.694 | AS2.703 | AS2.704 |
| AS2.1146 | | | | |

*Rhodotorula minuta* (Saito) Harrison

AS2.277

*Rhodotorula rubar* (Demme) Lodder

| AS2.21 | AS2.22 | AS2.103 | AS2.105 | AS2.108 |
|---|---|---|---|---|
| AS2.140 | AS2.166 | AS2.167 | AS2.272 | AS2.279 |
| AS2.282 | ACCC2031 | | | |

*Rhodotorula aurantiaca* (Saito) Lodder

| AS2.102 | AS2.107 | AS2.278 | AS2.499 | AS2.694 |
|---|---|---|---|---|
| AS2.703 | AS2.1146 | | | |

*Saccharomyces carlsbergensis* Hansen

| AS2.113 | ACCC2032 | ACCC2033 | AS2.312 | AS2.116 |
|---|---|---|---|---|
| AS2.118 | AS2.121 | AS2.132 | AS2.162 | AS2.189 |
| AS2.200 | AS2.216 | AS2.265 | AS2.377 | AS2.417 |
| AS2.420 | AS2.440 | AS2.441 | AS2.443 | AS2.444 |
| AS2.459 | AS2.595 | AS2.605 | AS2.638 | AS2.742 |
| AS2.745 | AS2.748 | AS2.1042 | | |

*Saccharomyces uvarum* Beijer

| IFFI1023 | IFFI1032 | IFFI1036 | IFFI1044 | IFFI1072 |
|---|---|---|---|---|
| IFFI1205 | IFFI1207 | | | |

*Saccharomyces willianus* Saccardo

| AS2.5 | AS2.7 | AS2.119 | AS2.152 | AS2.293 |
|---|---|---|---|---|
| AS2.381 | AS2.392 | AS2.434 | AS2.614 | AS2.1189 |

*Saccharomyces* sp.

AS2.311

*Saccharomycodes ludwigii* Hansen

ACCC2044  AS2.243  AS2.508

*Saccharomycodes sinenses* Yue

AS2.1395

*Schizosaccharomyces octosporus* Beijerinck

ACCC2046  AS2.1148

*Schizosaccharomyces pombe* Lindner

| ACCC2047 | ACCC2048 | AS2.214 | AS2.248 | AS2.249 |
|---|---|---|---|---|
| AS2.255 | AS2.257 | AS2.259 | AS2.260 | AS2.274 |
| AS2.994 | AS2.1043 | AS2.1149 | AS2.1178 | IFFI1056 |

*Sporobolomyces roseus* Kluyver et van Niel

| ACCC2049 | ACCC2050 | AS2.19 | AS2.962 | AS2.1036 |
|---|---|---|---|---|
| ACCC2051 | AS2.261 | AS2.262 | | |

*Torulopsis candida* (Saito) Lodder

AS2.270  ACCC2052

*Torulopsis famta* (Harrison) Lodder et van Rij

ACCC2053  AS2.685

*Torulopsis globosa* (Olson et Hammer) Lodder et van Rij

ACCC2054  AS2.202

TABLE 1-continued

Exemplary Yeast Strains

*Torulopsis inconspicua* Lodder et Kreger van Rij

AS2.75

*Trichosporon behrendii* Lodder et Kreger van Rij

ACCC2056 AS2.1193
*Trichosporon capitatum* Diddens et Lodder

ACCC2056 AS2.1385
*Trichosporon cutaneum* (de Beurm et al.) Ota

ACCC2057 AS2.25   AS2.570   AS2.571   AS2.1374
*Wickerhamia fluorescens* (Soneda) Soneda

ACCC2058 AS2.1388

II. Application of Electromagnetic Fields

An electromagnetic field useful in this invention can be generated and applied by various means well known in the art. For instance, the EMF can be generated by applying an alternating electric field or an oscillating magnetic field.

Alternating electric fields can be applied to cell cultures through electrodes in direct contact with the culture medium, or through electromagnetic induction. See, e.g., FIG. 1. Relatively high electric fields in the medium can be generated using a method in which the electrodes are in contact with the medium. Care must be taken to prevent electrolysis at the electrodes from introducing undesired ions into the culture and to prevent contact resistance, bubbles, or other features of electrolysis from dropping the field level below that intended. Electrodes should be matched to their environment, for example, using Ag-AgCl electrodes in solutions rich in chloride ions, and run at as low a voltage as possible. For general review, see Goodman et al., *Effects of EMF on Molecules and Cells*, International Review of Cytology, A, Survey of Cell Biology, Vol. 158, Academic Press, 1995.

The EMFs useful in this invention can also be generated by applying an oscillating magnetic field. An oscillating magnetic field can be generated by oscillating electric currents going through Helmholtz coils. Such a magnetic field in turn induces an electric field.

The frequencies of EMFs useful in this invention range from about 9500–13000 MHz (e.g., 9750–10500, 12000–12500 and/or 12600–12980 MHz). Exemplary frequencies are 10102, 10114, 12237, 12877, and 12895 MHz. The field strength of the electric field useful in this invention ranges from about 220 to 480 mV/cm (e.g., 250–270, 260–280, 280–305, 290–310, 315–335, 325–345, 350–370, 370–390, 380–400, 380–420, and/or 430–450 mV/cm). Exemplary field strengths are 250, 278, 280, 307, 321, 334, 352, 353, 372, 377, 385, 406, and 438 mV/cm.

When a series of EMFs are applied to a yeast culture, the yeast culture can remain in the same container while the same set of EMF generator and emitters is used to change the frequency and/or field strength. The EMFs in the series can each have a different frequency or a different field strength; or a different frequency and a different field strength. Such frequencies and field strengths are preferably within the above-described ranges. Although any practical number of EMFs can be used in a series, it may be preferred that the yeast culture be exposed to a total of 2, 3, 4, 5, 6, 7, 8, 9, 10, 11, 12, 13 or more EMFs in a series. In one embodiment, the yeast culture is exposed to a series of EMFs, wherein the frequency of the electric field is alternated in the range of about 9750–10500, 12000–12500 and 12600–12980 MHz.

Although the yeast cells can be activated after even a few hours of culturing in the presence of an EMF, it may be preferred that the activated yeast cells be allowed to multiply and grow in the presence of the EMF(s) for a total of 30–200 hours (e.g., 35–100 hours).

Figure 1:
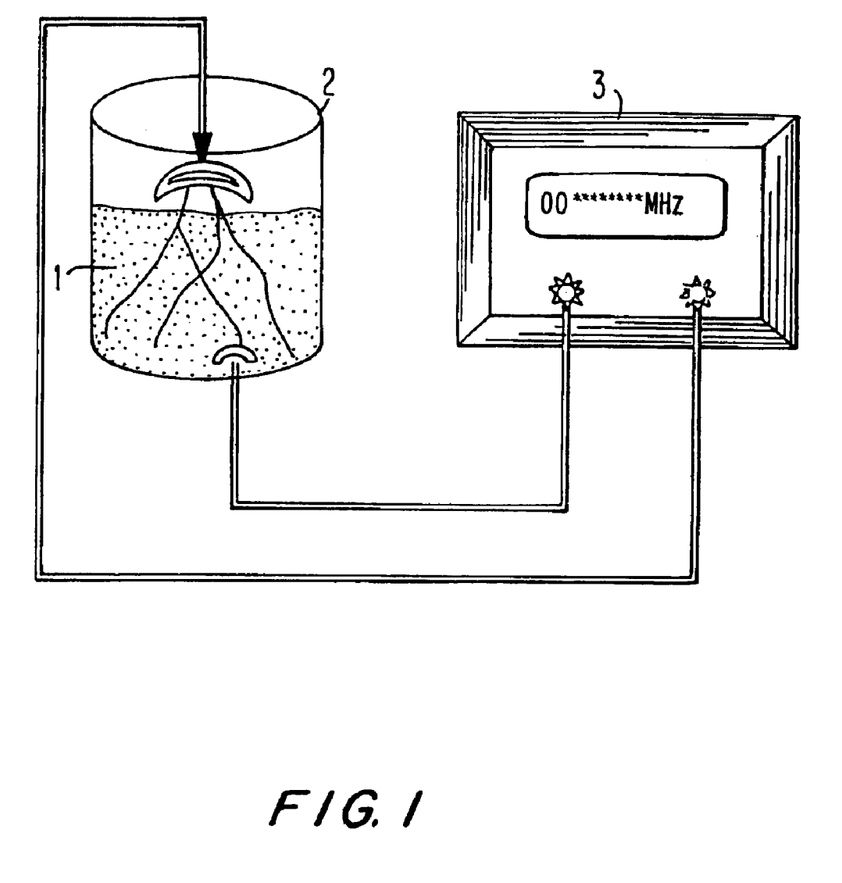
FIG. 1 is a schematic diagram showing an exemplary apparatus for activating yeast cells using electromagnetic fields. 1: yeast culture; 2: container; 3: power supply.

FIG. 1 illustrates an exemplary apparatus for generating alternating electric fields. An electric field of a desired frequency and intensity is generated by an AC source (3) capable of generating an alternating electric field, preferably in a sinusoidal wave form, in the frequency range of 10 to 20,000 MHz. Signal generators capable of generating signals with a narrower frequency range can also be used. If desirable, a signal amplifier can also be used to increase the output.

The activation container (2) can be made from non-conductive material, for example, plastics, glass steel, ceramic, and combinations thereof. The wire connecting the activation container (2) and the signal generator (3) is preferably a high frequency coaxial cable with a transmission frequency of at least 30 GHz.

The alternating electric field can be applied to the culture by a variety of means, including placing the yeast culture (1) in close proximity to the signal emitters such as a metal wire or tube capable of transmitting EMFs. The metal wire or tube can be made of red copper, and be placed inside the container (2), reaching as deep as 3–30 cm. For example, if the fluid in the container (2) has a depth of 15–20 cm, 20–30 cm, 30–50 cm, 50–70 cm, 70–100 cm, 100–150 cm or 150–200 cm, the metal wire can be 3–5 cm, 5–7 cm, 7–10 cm, 10–15 cm, 15–20 cm, 20–30 cm and 25–30 cm from the bottom of the container (2), respectively. The number of electrode wires used depends on the volume of the culture as well as the diameter of the wires. The number of metal wires/tubes used can be from 1 to 10 (e.g., 2 to 3). It is recommended, though not mandated, that for a culture having a volume up to 10 L, metal wires/tubes having a diameter of 0.5 to 2.0 mm be used. For a culture having a volume between 10 L and 100 L, metal wires/tubes having a diameter of 3.0 to 5.0 mm can be used. For a culture having a volume in the range of 100–1000 L, metal wires/tubes having a diameter of 6.0 to 15.0 mm can be used. For a culture having a volume greater than 1000 L, metal wires/tubes having a diameter of 20.0 to 25.0 mm can be used.

In one embodiment, the electric field is applied by electrodes submerged in the culture (1). In this embodiment, one of the electrodes can be a metal plate placed on the bottom of the container (2), and the other electrode can comprise a plurality of electrode wires evenly distributed in the culture (1) so as to achieve even distribution of the electric field energy. The number of electrode wires used depends on the volume of the culture as well as the diameter of the wires.

III. Culture Media

Culture media useful in this invention contain sources of nutrients assimilable by yeast cells. Complex carbon-containing substances in a suitable form, such as carbohydrates (e.g., sucrose, glucose, fructose, dextrose, maltose, xylose, cellulose, starches, etc.) and coal, can be the carbon sources for yeast cells. The exact quantity of the carbon sources utilized in the medium can be adjusted in accordance with the other ingredients of the medium. In general, the amount of carbohydrates varies between about 0.1% and 10% by weight of the medium and preferably between about 0.1% and 5% (e.g., about 2%). These carbon sources can be used individually or in combination. Amino acid-containing substances in suitable form (e.g., beef extract and peptone) can also be added individually or in combination. In general, the amount of amino acid containing substances varies between about 0.1% and 0.5% by weight of the medium and preferably between about 0.1% and 0.3% (e.g., about 0.25%). Among the inorganic salts which can be added to the culture medium are the customary salts capable of yielding sodium, potassium, calcium, phosphate, sulfate, carbonate, and like ions. Non-limiting examples of nutrient inorganic salts are $(NH_4)_2HPO_4$, $KH_2PO_4$, $K_2HPO_4$, $CaCO_3$, $MgSO_4$, $NaCl$, and $CaSO_4$.

IV. Electromagnetic Activation of Yeast Cells

To activate or enhance the ability of yeast cells to produce substances beneficial for renal functions (e.g., increasing urine secretion and/or lowering of blood urea nitrogen, proteinuria and/or serum creatinine levels), yeast cells of this invention can be activated by being cultured in an appropriate medium under sterile conditions at 20° C.–38° C., preferably at 28–32° C. (e.g., 30° C.) for a sufficient amount of time, e.g., 130–230 hours (e.g., 169–193 hours), in an alternating electric field or a series of alternating electric fields as described above.

An exemplary culture medium is made by mixing 1000 ml of distilled water with 18 g of mannitol, 40 μg of vitamin $B_3$, 30 μg of vitamin $B_{12}$, 10 μg of vitamin H, 35 ml of fetal bovine serum, 0.20 g of $KH_2PO_4$, 0.25 g of $MgSO_4 \cdot 7H_2O$, 0.3 g of NaCl, 0.2 g of $CaSO_4 \cdot 2H_2O$, 4.0 g of $CaCO_3 \cdot O5H_2O$, and 2.5 g of peptone.

An exemplary set-up of the culturing process is depicted in FIG. 1. Untreated yeast cells are added to a culture medium at $1 \times 10^8$ cells per 1000 ml of the culture medium. The yeast cells may be *Saccharomyces cerevisiae* Hansen AS2.504 or AS2.16, or may be selected from any of the strains listed in Table 1. An exemplary activation process of the yeast cells involves the following sequence: the yeast cells are grown in the culture medium for 26–30 hours (e.g., 28 hours) at 28–32° C. and then exposed to (1) an alternating electric field having a frequency of 10102 MHz and a field strength in the range of 260–280 mV/cm (e.g., 278 mV/cm) for 14–18 hours (e.g., 16 hours); (2) then to an alternating electric field having a frequency of 10114 MHz and a field strength in the range of 290–310 mV/cm (e.g., 307 mV/cm) for 34–38 hours (e.g., 36 hours); (3) then to an alternating electric field having a frequency of 12237 MHz and a field strength in the range of 325–345 mV/cm (e.g., 334 mV/cm) for 42–46 hours (e.g., 44 hours); (4) then to an alternating electric field having a frequency of 12877 MHz and a field strength in the range of 350–370 mV/cm (e.g., 353 mV/cm) for 37–41 hours (e.g., 39 hours); and (5) finally to an alternating electric field having a frequency of 12895 MHz and a field strength in the range of 280–305 mV/cm (e.g., 280 mV/cm) for 16–20 hours (e.g., 18 hours). The activated yeast cells are then recovered from the culture medium by various methods known in the art, dried (e.g., by lyophilization) and stored at about 4° C. in powder form. The resultant yeast powder preferably contains more than $10^{10}$ cells/g.

Subsequently, the activated yeast cells can be measured for their ability to treat kidney diseases (e.g., improve kidney functions) using standard methods known in the art, such as those described in Section VII.

V. Acclimatization of Yeast Cells to the Gastric Environment

Because the activated yeast cells of this invention must pass through the stomach before reaching the small intestine, where the effective components are released from these yeast cells, it is preferred that these yeasts be cultured under acidic conditions so as to acclimatize the cells to the gastric juice. This acclimatization process results in better viability of the yeast cells in the acidic gastric environment.

To achieve this, the yeast powder containing activated yeast cells can be mixed with a highly acidic acclimatizing culture medium at 10 g (containing more than $10^{10}$ activated cells per gram) per 1000 ml. The yeast mixture can then be cultured first in the presence of an alternating electric field having a frequency of 12877 MHz and a field strength in the range of 370–390 mV/cm (e.g., 377 mV/cm) at about 28 to 32° C. for 42–48 hours (e.g., 46 hours). The resultant yeast cells can then be further incubated in the presence of an alternating electric field having a frequency of 12895 MHz and a field strength in the range of 350–370 mV/cm (e.g., 352 mV/cm) at about 28 to 32° C. for 15–25 hours (e.g., 20 hours). The resulting acclimatized yeast cells are then recovered from the culture medium by various methods known in the art and are dried and stored either in powder form ($\geq 10^{10}$ cells/g) at room temperature or in vacuum at 0–4° C.

An exemplary acclimatizing culture medium is made by mixing 700 ml fresh pig gastric juice and 300 ml wild Chinese hawthorn extract. The pH of acclimatizing culture medium is adjusted to 2.5 with 0.1 M hydrochloric acid (HCl) and 0.2 M potassium hydrogen phthalate ($C_6H_4$(COOK)COOH). The fresh pig gastric juice is prepared as follows. At about 4 months of age, newborn Holland white pigs are sacrificed, and the entire contents of their stomachs are retrieved and mixed with 2000 ml of water under sterile conditions. The mixture is then allowed to stand for 6 hours at 4° C. under sterile conditions to precipitate food debris. The supernatant is collected for use in the acclimatizing culture medium. To prepare the wild Chinese hawthorn extract, 500 g of fresh wild Chinese hawthorn is dried under sterile conditions to reduce water content ($\geq 8\%$). The dried fruit is then ground ($\geq 20$ mesh) and added to 1500 ml of sterile water. The hawthorn slurry is allowed to stand for 6 hours at 4° C. under sterile conditions. The hawthorn supernatant is collected to be used in the acclimatizing culture medium.

VI. Manufacture of Yeast Compositions

Figure 2:
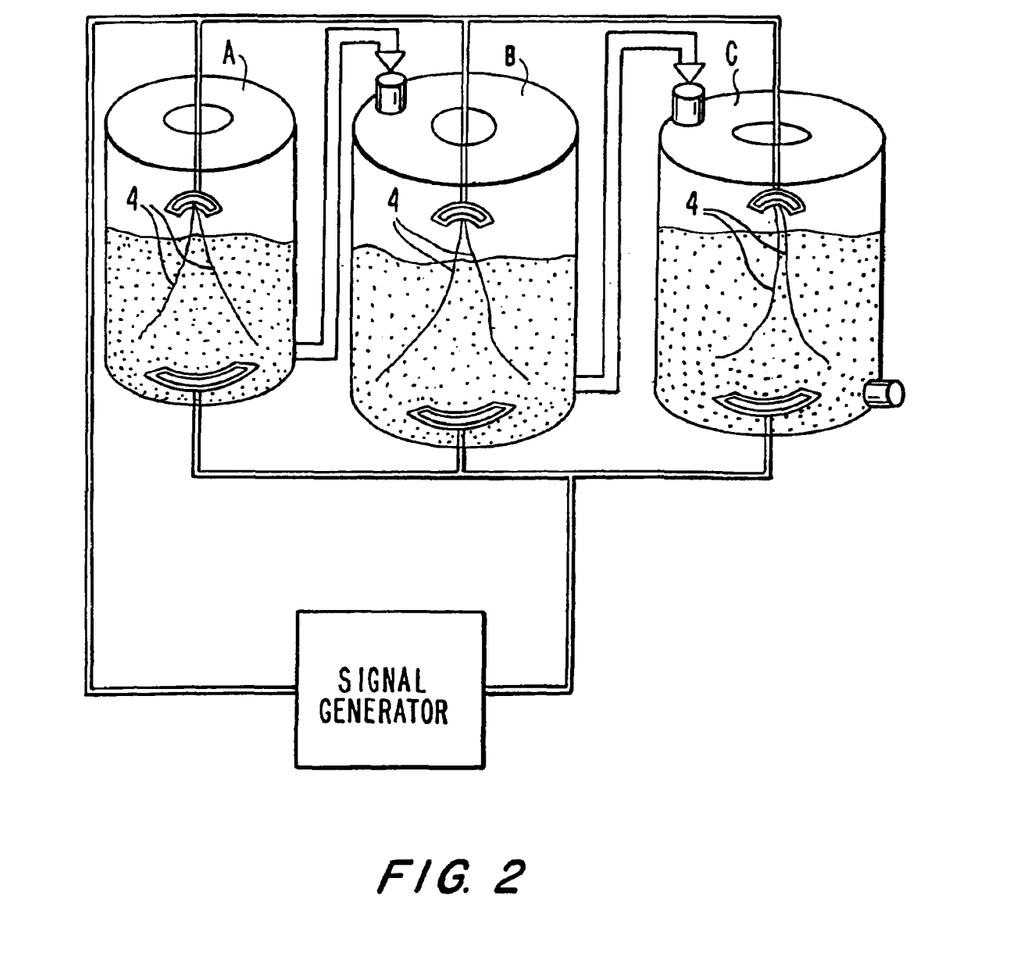
FIG. 2 is a schematic diagram showing an exemplary apparatus for making yeast compositions of the invention. The apparatus comprises a signal generator (such as models 83721B and 83741A manufactured by HP) and interconnected containers A, B and C.

To prepare the yeast compositions of the invention, an apparatus depicted in FIG. 2 or an equivalent thereof can be used. This apparatus includes three containers, a first container (A), a second container (B), and a third container (C), each equipped with a pair of electrodes (4). One of the electrodes is a metal plate placed on the bottom of the containers, and the other electrode comprises a plurality of electrode wires evenly distributed in the space within the container to achieve even distribution of the electric field energy. All three pairs of electrodes are connected to a common signal generator.

The culture medium used for this purpose is a mixed fruit extract solution containing the following ingredients per 1000 L: 300 L of wild Chinese hawthorn extract, 300 L of jujube extract, 300 L of *Schisandra chinensis* (*Turez*) *Baill* seeds extract, and 100 L of soy bean extract. To prepare hawthorn, jujube and *Schisandra chinensis* (*Turez*) *Baill* seeds extracts, the fresh fruits are washed and dried under sterile conditions to reduce the water content to no higher than 8%. One hundred kilograms of the dried fruits are then ground ($\geq 20$ mesh) and added to 400 L of sterile water. The mixtures are stirred under sterile conditions at room temperature for twelve hours, and then centrifuged at 1000 rpm to remove insoluble residues. To make the soy bean extract, fresh soy beans are washed and dried under sterile conditions to reduce the water content to no higher than 8%. Thirty kilograms of dried soy beans are then ground into particles of no smaller than 20 mesh, and added to 130 L of sterile water. The mixture is stirred under sterile conditions at room temperature for twelve hours and centrifuged at 1000 rpm to remove insoluble residues. Once the mixed fruit extract solution is prepared, it is autoclaved at 121° C. for 30 minutes and cooled to below 40° C. before use.

One thousand grams of the activated yeast powder prepared as described above (Section V, supra) is added to 1000 L of the mixed fruit extract solution, and the yeast solution is transferred to the first container (A) shown in FIG. 2. The yeast cells are then cultured in the presence of an alternating electric field having a frequency of 12877 MHz and a field strength of about 380–420 mV/cm (e.g., 406 mV/cm) at 28–32° C. under sterile conditions for 32 hours. The yeast cells are further incubated in an alternating electric field having a frequency of 12895 MHz and a field strength of 370–390 mV/cm (e.g., 372 mV/cm). The culturing continues for another 12 hours at 28–32° C.

The yeast culture is then transferred from the first container (A) to the second container (B) (if need be, a new batch of yeast culture can be started in the now available the first container (A)), and subjected to an alternating electric field having a frequency of 12877 MHz and a field strength of 430450 mV/cm (e.g., 438 mV/cm) for 24 hours at 28–32° C. Subsequently the frequency and field strength of the electric field are changed to 12895 MHz and 380–400 mV/cm (e.g., 385 mV/cm), respectively. The culturing process continues for another 12 hours at 28–32° C.

The yeast culture is then transferred from the second container (B) to the third container (C), and subjected to an alternating electric field having a frequency of 12877 MHz and a field strength of 315–335 mV/cm (e.g., 321 mV/cm) for 24 hours. Subsequently the frequency and field strength of the electric field are changed to 12895 MHz and 250–270 mV/cm (e.g., 250 mV/cm), respectively. The culturing continues for another 12 hours.

The yeast culture from the third container (C) can then be packaged into vacuum sealed bottles for use as medication or dietary supplement, e.g., in the form of health drinks, pills, or powder, etc. If desired, the final yeast culture can also be dried within 24 hours and stored in powder form. The dietary supplement can be taken three to four times daily at 30–60 ml per dose for a three-month period, preferably 10–30 minutes before meals and at bedtime.

In some embodiments, the compositions of the invention can also be administered intravenously or peritoneally in the form of a sterile injectable preparation. Such a sterile preparation can be prepared as follows. A sterilized health drink composition is first treated under ultrasound ($\geq 18,000$ Hz) for 10 minutes and then centrifuged for another 10 minutes. The resulting supernatant is adjusted to pH 7.2–7.4 using 1 M NaOH and subsequently filtered through a membrane (0.22 $\mu$m for intravenous injection and 0.45 $\mu$m for peritoneal injection) under sterile conditions. The resulting sterile preparation is submerged in a 35–38° C. water bath for 30 minutes before use. In other embodiments, the compositions of the invention may also be formulated with pharmaceutically acceptable carriers to be orally administered in any orally acceptable dosage form including, but not limited to, capsules, tablets, suspensions or solutions.

The yeast compositions of the present invention are derived from yeasts used in food and pharmaceutical industries. The yeast compositions are thus devoid of side effects associated with many conventional pharmaceutical compounds.

VII. Examples

In order that this invention be more fully understood, the following examples are set forth. These examples are for the purpose of illustration only and are not to be construed as limiting the scope of the invention in any way.

The activated yeast compositions used in the following examples were prepared as described above, using *Saccharomyces cerevisiae* Hansen AS2.16 cells, cultured in the presence of an alternating electric field having the electric field frequency and field strength exemplified in the parentheses following the recommended ranges listed in Section IV, supra. Control (i.e., untreated) yeast compositions were those prepared in the same manner as described in Section VI, supra, except that the yeast cells were cultured in the absence of EMFs. All compositions of interest were administered to the animals by intragastric feeding, unless otherwise specified.

Example 1

Effects of Treatment on Renal Failure in Rats

To test the ability of the EMF-treated AS2.16 cells to ameliorate renal failure and restore renal function, forty healthy male Wistar rats (3–6 months old, about 180 to 200 g body weight) were selected and randomly divided into four equal groups, Groups A, B, C and D. Group D rats were used as controls. Under anesthesia with amobarbital (3.0 ml/100 g body weight), each of Groups A, B and C rats was laid prone on an operating table and its posterior abdominal cavity was opened under sterile conditions. The right kidney was exposed and two thirds of the cortical tissue (about 0.45–5.0 g) of the right kidney were removed. After bleeding was stopped, the muscular tissue was injected with penicillin ($1.5 \times 10^4$ units/100 g body weight) to prevent infection. The wound opening was then closed by stitches. One week later, blood samples were collected from the tail and the carotid artery of each rat in the four groups ten hours after feeding with water only. Blood urea nitrogen (BUN) and serum creatinine levels in the blood samples were determined for all rats. Urine samples from each rat in the four groups were collected for a twenty-four hour period, during which the rat was given water but no food. The collected urine samples were preserved with xylene and the proteinuria concentration in the samples was determined. Subsequently, the abdominal cavity of each of Groups A, B and C rats was re-opened by the same method as described above. The renal pedicel was ligated with a ligature and the left kidney was removed. All rats in the four groups were then raised with normal feed for another week.

At week three, a composition of interest (1.5 ml/100 g body weight) was administered to each of the operated rats once daily for the next eight weeks. Rats in Group A were each given the activated yeast composition at a dose of 1.5 ml/100 g body weight. Rats in Groups B and C were treated in the same manner as those in Group A, except that they were given the control yeast composition and tap water, respectively, in lieu of the activated yeast composition. Rats in Group D were treated in the same manner as those in Group C, except that the former were not operated on. Urine samples were collected for a twenty-four hour period and the proteinuria concentration was determined. BUN levels and serum creatinine readings in the blood samples were also determined as described above. The results were summarized in Tables 2 and 3.

TABLE 2

Urine Secretion of Male Wistar Rats.

| | Urine (ml, for a 24 hour period) | | Proteinuria (mg, for a 24 hour period) | |
|---|---|---|---|---|
| Grp. | Prior to Administration (week 2) | After Administration (week 11) | Prior to Administration (week 2) | After Administration (week 11) |
| A | 8.3 ± 2.3 | 25.6 ± 3.5 | 9.3 ± 3.3 | 6.7 ± 3.4 |
| B | 11.3 ± 3.4 | 11.7 ± 3.3 | 11.2 ± 3.8 | 18.6 ± 6.4 |
| C | 11.2 ± 3.2 | 11.6 ± 3.6 | 10.9 ± 4.1 | 19.3 ± 5.7 |
| D | 5.1 ± 2.2 | 9.4 ± 2.9 | 5.2 ± 2.2 | 5.8 ± 3.6 |

TABLE 3

Serum BUN and Creatinine Levels of Male Wistar Rats.

| | BUN (mM) | | Serum Creatinine (mM) | |
|---|---|---|---|---|
| Group | Prior to Administration | After Administration | Prior to Administration | After Administration |
| A | 19.6 ± 4.4 | 7.6 ± 0.7 | 103.6 ± 12.4 | 46.3 ± 7.7 |
| B | 18.4 ± 4.3 | 19.7 ± 3.8 | 99.6 ± 14.2 | 169.8 ± 23.4 |
| C | 18.8 ± 3.3 | 17.9 ± 3.6 | 103.4 ± 14.5 | 172.3 ± 22.8 |
| D | 7.5 ± 0.6 | 3.8 ± 2.9 | 26.7 ± 4.4 | 33.7 ± 10.6 |

The above results show that the activated yeast composition increased urine secretion, decreased proteinuria concentration, and lowered BUN and serum creatinine levels. In contrast, the control yeast composition demonstrated no such effects.

Additionally, rats given the activated yeast composition showed noticeable improvement in the amount of food intake which resulted in an increase in body weight.

Example 2

Diuretic Effect in Rabbits

To test the diuretic effect of the EMF-treated AS2.16 cells, each of eighteen healthy domesticated male rabbits (*Oryctolagus curiculus*, 3–5 months old, about 2±0.2 kg body weight) was injected with 5% glucose saline (10 ml/kg) through the marginal vein of its ear. A urinary catheter was gently inserted into the rabbit's bladder for 8–10 cm. The bladder was emptied and urine was collected twice, each for a period of 5 to 10 minutes. The collected urine samples were measured and recorded. Another catheter was subsquently inserted into the rabbit's stomach. The rabbits were then randomly divided into three equal groups.

A composition of interest (12 ml/kg) was fed to each rabbit through the catheter to the stomach. Rabbits in Group A were each given the activated yeast composition at a dose of 12 ml/kg body weight. Rabbits in Groups B and C were treated in the same manner as those in Group A, except that they were given the control yeast composition and saline, respectively, in lieu of the activated yeast composition. Urine samples were collected every 30 minutes for three times starting 30 minutes after the administration. These results were summarized in Table 4.

TABLE 4

Effects of Treatment on Urine Secretion.

| | Urine (ml) | | | |
|---|---|---|---|---|
| | Before Administration | After Administration | | |
| Group | (0 minutes) | 30 minutes | 60 minutes | 90 minutes |
| A | 0.6 ± 0.3 | 7.8 ± 2.6 | 12.7 ± 1.9 | 13.8 ± 2.2 |
| B | 0.6 ± 0.3 | 2.4 ± 1.7 | 3.7 ± 2.3 | 3.9 ± 2.1 |
| C | 0.7 ± 0.2 | 2.3 ± 1.4 | 3.5 ± 2.1 | 4.1 ± 1.9 |

The above results show that the activated composition increased urine secretion compared to the controls.

While a number of embodiments of this invention have been set forth, it is apparent that the basic constructions may be altered to provide other embodiments which utilize the compositions and methods of this invention.

What is claimed is:

1. A composition comprising a plurality of yeast cells, wherein said plurality of yeast cells are characterized by their ability to treat renal failure in a subject, said ability resulting from their having been cultured in the presence of an alternating electric field having a frequency in the range of about 9500 to 13000 MHz and a field strength in the range of about 220 to 480 mV/cm, as compared to yeast cells not having been so cultured.

2. The composition of claim 1, wherein said frequency is in the range of about 9750–10500, 12000–12500 or 12600–12980 MHz.

3. The composition of claim 1, wherein said field strength is in the range of about 250–270, 260–280, 280–305, 290–310, 315–335, 325–345, 350–370, 370–390, 380–400, 380–420, or 430–450 mV/cm.

4. The composition of claim 1, wherein said yeast cells are cells of the species *Saccharomyces cerevisiae*, *Saccharomyces carlsbergensis*, *Saccharomyces rouxii*, *Saccharomyces sake*, *Saccharomyces uvarum*, *Saccharomyces sp.*, *Schizosaccharomyces pombe*, *Rhodotorula aurantiaca*, or *Rhodotorula rubar*.

5. The composition of claim 1, wherein said yeast cells are derived from cells of the strain deposited at the China General Microbiological Culture Collection Center with an accession number selected from the group consisting of *Saccharomyces cerevisiae* Hansen AS2.16, AS2.112 and AS2.504, *Saccharomyces sp.* AS2.311, *Schizosaccharomyces pombe* Lindner AS2.274, *Saccharomyces sake* Yabe ACCC2045, *Saccharomyces uvarum* Beijer IFFI1207, *Saccharomyces rouxii* Boutroux AS2.370, *Saccharomyces cerevisiae* Hansen Var. *ellipsoideus* AS2.612, *Saccharomyces carlsbergensis* Hansen AS2.417, and *Rhodotorula rubar* (Demme) Lodder AS2.105.

6. The composition of claim 1, wherein said composition is in the form of a tablet, powder, or a health drink.

7. The composition of claim 6, wherein said composition is in the form of a health drink.

8. A method for improving kidney functions in a subject comprising administering to said subject a composition of claim 1.

9. The method of claim 8 comprising oral administration.

10. A method of preparing a yeast composition, comprising culturing a plurality of yeast cells in the presence of an alternating electric field having a frequency in the range of about 9500 to 13000 MHz and a field strength in the range of about 220 to 480 mV/cm, wherein said composition is capable of treating renal failure in a subject as compared to yeast cells not having been so cultured.

11. The composition of claim 10, wherein said frequency is in the range of about 9750–10500, 12000–12500 or 12600–12980 MHz.

* * * * *

UNITED STATES PATENT AND TRADEMARK OFFICE
CERTIFICATE OF CORRECTION

PATENT NO. : 6,913,913 B2
DATED : July 5, 2005
INVENTOR(S) : Ling Yuk Cheung

Page 1 of 1

It is certified that error appears in the above-identified patent and that said Letters Patent is hereby corrected as shown below:

Column 2,
Line 41, change "carisbergensis" to -- carlsbergensis --.

Column 9,
Line 24, change "$CaCO_3$ $05H_2O$" to -- $CaCO_3$ $5H_2O$ --.

Column 10,
Line 28, change "$\geq 8\%$" to -- $\leq 8\%$ --.

Column 11,
Line 18, change "430450" to -- 430-450 --.

Column 13,
Line 55, change "subsquently" to -- subsequently --.

Signed and Sealed this

Third Day of January, 2006

JON W. DUDAS
*Director of the United States Patent and Trademark Office*